United States Patent
Christensen et al.

(10) Patent No.: US 7,918,718 B2
(45) Date of Patent: Apr. 5, 2011

(54) METHOD AND FACILITY FOR AUTOMATICALLY DETERMINING QUALITY CHARACTERISTICS OF A CARCASS ON A SLAUGHTERLINE

(75) Inventors: Lars Bager Christensen, Gadstrup (DK); Eli Vibeke Olsen, Roskilde (DK)

(73) Assignee: Slagteriernes Forskningsinstitut, Roskilde (DK)

( * ) Notice: Subject to any disclaimer, the term of this patent is extended or adjusted under 35 U.S.C. 154(b) by 442 days.

(21) Appl. No.: 11/915,962

(22) PCT Filed: May 24, 2006

(86) PCT No.: PCT/DK2006/000283
§ 371 (c)(1), (2), (4) Date: Mar. 19, 2008

(87) PCT Pub. No.: WO2006/128456
PCT Pub. Date: Dec. 7, 2006

(65) Prior Publication Data
US 2008/0200107 A1   Aug. 21, 2008

(30) Foreign Application Priority Data
May 31, 2005   (DK) .................................. 2005 00791

(51) Int. Cl.
*A22C 18/00* (2006.01)
(52) U.S. Cl. ....................................................... 452/157
(58) Field of Classification Search .................. 452/157, 452/158; 358/93; 382/110, 194, 195
See application file for complete search history.

(56) References Cited

U.S. PATENT DOCUMENTS

| | | | |
|---|---|---|---|
| 4,241,473 A | 12/1980 | Korhonen | |
| 5,314,375 A * | 5/1994 | O'Brien et al. | 452/157 |
| 5,334,084 A * | 8/1994 | O'Brien et al. | 452/157 |
| 5,668,634 A | 9/1997 | Newman | |
| 5,793,879 A | 8/1998 | Benn et al. | |
| RE36,664 E * | 4/2000 | O'Brien et al. | 452/157 |
| 6,198,834 B1 | 3/2001 | Belk et al. | |
| 6,609,423 B1 * | 8/2003 | Retterath et al. | 73/433 |
| 6,735,326 B1 * | 5/2004 | Schimitzek | 382/110 |
| 6,829,927 B2 * | 12/2004 | Retterath et al. | 73/149 |
| 6,891,961 B2 * | 5/2005 | Eger et al. | 382/110 |
| 6,974,373 B2 * | 12/2005 | Kriesel | 452/157 |
| 7,128,024 B2 * | 10/2006 | Doyle, II | 119/518 |
| 7,214,128 B2 * | 5/2007 | Kriesel | 452/157 |
| 7,347,161 B2 * | 3/2008 | Pratt | 119/51.02 |
| 7,399,220 B2 * | 7/2008 | Kriesel et al. | 452/157 |
| 2007/0275647 A1 | 11/2007 | Eger | |

FOREIGN PATENT DOCUMENTS

| | | |
|---|---|---|
| DE | 102004047773 A1 | 4/2006 |
| EP | 1135988 A2 | 9/2001 |
| GB | 2285126 A | 6/1995 |
| WO | WO 9205703 A1 | 4/1992 |

\* cited by examiner

Primary Examiner — Thomas Price
(74) Attorney, Agent, or Firm — Sughrue Mion, PLLC (57) ABSTRACT

A method for automatically determining quality characteristics of a carcass on a slaughterline. The method comprises conveying the carcass in a direction of transport, preliminary examination to determine the location of one or more anatomical reference parts of the carcass in the direction of transport, calculating the location in the direction of transport of at least one cross-section in the carcass using the location of the anatomical reference part(s) and possibly other data on the carcass, and CT measuring the nature of internal anatomical parts of the carcass in at least one of these cross-sections in the carcass, controlled by the calculated location.

9 Claims, 8 Drawing Sheets

METHOD AND FACILITY FOR AUTOMATICALLY DETERMINING QUALITY CHARACTERISTICS OF A CARCASS ON A SLAUGHTERLINE

The present invention relates to a method and a facility for automatically determining quality characteristics of a carcass on a slaughterline.

In slaughterhouses, carcasses are examined and processed based on on-line measurement of individual carcasses. To determine the quality and/or to cut the carcass into valuable parts, the examination and processing devices are controlled relative to the location of anatomical parts of the carcass.

Prior art comprises mechanical detection of external anatomical parts where a mechanical sensor detects an accessible anatomical part, such as a foreleg on the carcass.

Prior art further comprises photographic surface measurement of visible anatomical parts where scaled standard images of known anatomical external parts are compared to an image of a carcass in order to recognize and localize an external anatomical part of the carcass.

To be able to measure important quality characteristics of carcasses, it is necessary to measure internal anatomical parts of carcasses. The back fat thickness may be measured sing ultrasound. However, ultrasound requires achievement of good contact between the ultrasound transducer and the carcass, which may be difficult to achieve for an automatic on-line system. Ultrasound and other known on-line systems for measuring internal parts are relatively inaccurate and are, in many instances, not able to measure certain desired quality parameters of carcasses.

WO 92/05703 A1 discloses a method and a device for cutting food products. The food product is scanned using NMR or X-ray, and distribution of different types of tissue in the product is determined on the basis of the signal information obtained in the scanning. Positions of suitable cuts in the product are determined.

WO 2006/034871 A1, having a publication date after the priority date of the present application, relates to a method for determining physiological parameters of a carcass using computed tomography.

It is thus an object of the invention to provide a method and a facility with an improved procedure or technique for automatically determining quality characteristics of a carcass on a slaughterline based on a measurement of internal anatomical parts.

The method of the invention comprises:
a) conveying the carcass in a direction of transport,
b) preliminary examination to determine the location of one or more anatomical reference arts of the carcass in the direction of transport,
c) calculating the location in the direction of transport of at least one cross-section in the carcass suited for CT measurement using the location of the anatomical reference parts and possibly other data on the carcass, and
d) CT measuring the nature of internal anatomical parts of the carcass in at least one of these cross-sections in the carcass, controlled by the calculated location.

Preferred embodiments of the method of the invention are stated in claims 2-4.

The location in the direction of transport of a reference part of the carcass may thus be determined by means of a detector for an external or internal anatomical part of the carcass. Suitable measuring principles comprise mechanical, optical or radiation-based measurement.

For the determination of the location of the reference part(s) with penetrating radiation, the transmitted and/or scattered radiation may, after having left the carcass, be measured in at least one direction so that internal anatomical parts may be analysed and the location of the reference part(s) may be determined.

The reference part(s) may comprise an externally detectable anatomical part, including a foreleg, an elbow, an armpit, a groin, a tail/tail head or a pubic bone.

The location in the direction of transport of the at least one cross-section of the carcass may be calculated by means of an algorithm or a model using the location of the reference part(s), e.g. from known and/or calibrated distances between anatomical parts on corresponding carcasses of known build. For example, it is known that the internal anatomical part M. Longissimus Dorsi for a standard slaughter pig of the type Landrace-Duroc-Yorkshire, LDY cross, of 100 kg is in a range extending about 20 to 80 cm in the longitudinal direction measured from the tail head, and that CT measurement may thus be made at one or more appropriate places between these extreme points when the position of the tail head is determined. With heavier or lighter animals the targets are changed, which must be considered when measuring on these animals.

The CT measurement of the nature of internal anatomical parts of the carcass may comprise measurement of less than 50% by volume of the carcass. Preferably, enough cross-sections may be measured to map out between 1 and 20% by volume of the nature of the carcass, from which the nature of other internal anatomical parts may be predicted with good accuracy by means of suitable models. In this way measuring time and wear and tear on CT measuring equipment is saved. At a slaughterline rate of 400 carcasses per hour not more than 9 seconds are available for carrying out CT measurement. If CT measuring equipment with a measuring time per cross-section of one second is used, one can count on being able to make e.g. 3-5 measurements per carcass in practice. These measurements are made so that the most interesting or telling internal parts are examined.

The CT measurement of the nature of internal anatomical parts of the carcass may comprise measurement in 2-50 cross-sections that are located at a mutual distance in the direction of transport of at least 2.5 cm, preferably at least 5 cm, without CT measurement between at least two of these cross-sections, or measurement in 2-50, preferably 2-16 cross-sections, that are located side-by-side at a mutual distance in the direction of transport mainly corresponding to the measuring width of a cross-section. In this embodiment, the rate of the slaughterline and the measuring rate of the measuring equipment will also be limiting for the number of cross-sections that can be examined per carcass. By placing the cross-sections close to each other, more detailed information on specific internal parts, e.g. on the location of certain bones, is obtained. This information may for instance be used during subsequent cutting of the carcass. The cross-sections may for instance be recorded by means of a scanner with several rows of detectors so that several cross-sections are recorded simultaneously when rotating X-ray source/detectors.

The obtained CT data may be processed by means of a computer program for determining quality characteristics of the carcass. Hereby, data may be isolated or processed which are interesting in relation to sought quality characteristics, and these may be used as an expression of the carcasses and be recorded in a database together with the identity of the carcass.

The CT measurement is made by means of CT measuring equipment, the structure and work principles of which is known and will thus not be described in detail hereafter. CT means computed tomography or computer tomographical.

Computed tomography is a radiological examination method where a circulating X-ray source and opposing detectors measure how much the measured object attenuates the X-radiation in different directions, and a computer calculates the attenuation in the individual parts of the measured object and carries out reconstruction calculations.

The CT examination may comprise determination of the attenuation of transmitted and/or scattered radiation, whereby a measure of how much the radiation intensity is attenuated is obtained by e.g. comparing the intensity of the radiation at the input and output of radiation.

The energy of the radiation may be of an appropriate, suitable magnitude. Several energies may be used at the same time. X-radiation may comprise one or more energies, so that e.g. energy dependent attenuation of different tissue types and tissue densities may be used to better distinguish between e.g. fatty tissue, muscular tissue and bone tissue.

By making measurements in several directions, e.g. from 0 to 180 degrees or from 0 to 360 degrees around a carcass, two-dimensional sectional images of the carcass are obtained after reconstruction from the measurements. By piecing together several of such sectional images for several positions relative to a reference part, a three-dimensional mapping of the internal anatomical parts of the carcass is obtained. If the cross-sections are dispersed, they may be compared to corresponding cross-sections in model carcasses that are e.g. obtained by complete CT scan of carcasses and have detailed data concerning e.g. their lean meat content etc. The model carcass that best corresponds to the found cross-sections may then be considered representative of the carcass in question. If the cross-sections are close to each other, they themselves give a detailed image of this part of the carcass. By this, accurate anatomical measurements for use in, e.g. determining quality characteristics, veterinary inspection and/or processing of the carcass, are obtained. The obtained anatomical measurements or quality characteristics may be used in subsequent processing of the carcass, e.g. for sorting and/or favourable cutting in predetermined parts that are optimally cut off in terms of e.g. price and customer wishes.

The carcass may, during preliminary examination and/or during CT measurement, be moving or resting.

The facility of the invention comprises:
a) a conveyor for conveying the carcass in a direction of transport,
b) a preliminary examination unit comprising devices for determining the location of one or more anatomical reference parts of the carcass in the direction of transport,
c) a calculation unit for calculating the location in the direction of transport of at least one cross-section in the carcass using the location of the anatomical reference part(s) and possibly other data on the carcass, and
d) CT measuring equipment for measuring the nature of internal anatomical parts of the carcass in at least one of these cross-sections in the carcass controlled by the calculated location.

Preferred embodiments of the facility according to of the invention are stated in claims 6 and 7.

The facility may comprise a detector for an external or internal part of the carcass to determine the location in the direction of transport of a reference part of the carcass.

The preliminary examination unit may be adapted for determining the location of one/more externally detectable anatomical part(s), including a foreleg, an elbow, an armpit, a groin, a tail/tail head, or a pubic bone.

The calculation unit may be adapted for calculating the location in the direction of transport of the at least one cross-section of the carcass by means of an algorithm or a model using the location of the reference part(s) and possibly other data for the carcass.

In the facility, CT measurement of the nature of internal anatomical parts of the carcass may comprise measurement of less than 50% by volume of the carcass, preferably between 1 and 20% by volume.

The facility may be adapted for CT measurement of the nature of internal anatomical parts of the carcass in 2-50 cross-sections that are located at a mutual distance in the direction of transport of at least 2.5 cm, preferably at least 5 cm, without CT measurement between at least two of these cross-sections, or in 2-50, preferably 2-16 cross-sections, that are located side-by-side at a mutual distance in the direction of transport essentially corresponding to the measuring width of a cross-section.

The facility may comprise devices for detecting the relative displacement of the reference part(s) of the carcass relative to the CT measuring equipment.

The facility may comprise devices for securing the carcass to a conveying member in the conveyor, e.g. to the belt of a belt conveyor, to a cart for the carcass or to gambrels that are transported by the slaughterline conveyor (overhead conveyor).

The facility may comprise a computer and a program for processing the obtained CT data in order to determine quality characteristics of the carcass.

The preliminary examination unit and the CT measuring equipment may be physically distinct units, making it possible to separate the preliminary examination and the CT measurement to different points of time and to different places, so that one does not become directly dependent on the other. Furthermore, the preliminary examination unit and the measuring equipment may be a physically combined unit. In both instances, as regards time, two carcasses may be preliminary examined and CT scanned at the same time, or somewhat apart from one another.

When the preliminary examination unit and the CT measuring equipment are contained in a common physical unit, a physically shorter distance between the two examinations is obtained, and thus a greater assurance that the anatomical reference part does not change its location during transport.

In a particular embodiment, the preliminary examination unit is physically directly leading on the slaughterline relative to the CT measuring equipment, so that the internal anatomical parts to be examined are not moved or are only moved a little relative to the reference part. For example, the preliminary examination unit measures an anatomical reference part on the carcass that is further ahead in the direction of transport, e.g. the tail head of a slaughter pig. The irradiation and detection devices are already placed in such a way that they, with only little time delay, commence irradiation and measurement on the desired site of the carcass relative to the reference part, e.g. at the groin.

The facility of the invention comprises devices for conveying the carcass through the CT measuring equipment, e.g. a conveyor belt or a piece of the slaughterline conveyor for gambrels with carcasses.

The facility comprises devices for detecting the relative displacement/movement of the reference part(s) of the carcass relative to the measuring area of the CT measuring equipment so that CT measurement is carried out in the calculated cross-sections of the carcass.

The facility may comprise devices for securing the carcass during transport and/or measurement.

To coordinate the operation of the preliminary examination unit and the CT measuring equipment, a control unit is preferably used, said control unit comprising:
a) a device for receiving signals from the preliminary examination unit and,
b) a device for processing and sending control signals to the CT measuring equipment, in order to set an irradiation and measuring point or an irradiation and measuring section for an internal part relative to the location of the reference part(s) of the carcass.

By means of the method and the facility of the invention, the location of one or more anatomical parts of a carcass and/or distribution of tissue types may be determined, and in this way a mapping of the carcass in one or more selected cross-sections in the carcass is achieved, which may be used as a basis for determining quality parameters, sorting and/or cutting or processing. Anatomical parts that are interesting in a slaughterhouse context are e.g. muscles, bones and fatty tissue, such as muscles in the ham and the loin, bones, e.g. ribs, and fatty tissue on ham, loin and belly, see e.g. the product catalogue of Danish Crown.

The method and the facility of the invention use CT measuring apparatus for determining the desired quality parameters of the carcass. Imaging of every cross-section of a carcass may thus be provided by reconstruction using projections of transmission or scatter data obtained by irradiating the carcass in one or more directions with a transmitting radiation.

Herein, carcass may mean a whole carcass, a half carcass, a front part, a back part or the front end, the middle or the ham piece of a three-piece half carcass or the loin piece or breast piece of a middle piece. The carcass may for instance be from pigs or cattle.

Herein, a part or a cut may mean a piece of meat, as known from slaughterhouses and meat processing companies, e.g. the loin (Longissimus Dorsi) or the ham.

The CT measurement may be performed as a slice measurement where there is no movement in the direction of transport between the measuring equipment and the carcass during measurement, or as a spiral measurement where there is movement in the direction of transport between measuring equipment and carcass during measurement.

According to the invention, CT data obtained on-line on a slaughterline on internal anatomical parts of carcasses in at least one cross-section of the carcass may be used for determining quality characteristics and/or sorting and/or processing of carcasses or parts thereof.

They may thus be used for determining lean meat content, muscular fullness, fat thickness, weight, or bone size and/or for separating, cutting or trimming, and/or for sorting or marking carcasses or parts thereof produced by separation and/or processing.

The invention thus has aspects of measuring technique as well as application within the meat industry.

One aspect of the present invention is to be able to plan, from measurements of internal parts, the most appropriate use of the carcass with regard to minimum waste, high demand and high price, or the very good selection of meat products produced from the carcass. By means of the measurements, which may for instance be CT measurements or other tomographical measurements in suitable cross-sections, ultrasonic measurements at appropriate places on the surface of the carcass, or possibly video recordings, images or information on the interior of the carcass should, according to the invention, be determined with such great accuracy that it is possible to be able to determine 3D models of the interesting internal parts of the carcass. The 3D models can be used for determining quality characteristics of predetermined parts (muscles, fat layer, etc.), such as the dimensions thereof.

This aspect is provided by a method for planning the production of meat products from carcasses on a slaughterline comprising:
a) measuring internal anatomical parts of the carcass,
b) determining quality characteristics of the carcass based on the measurements,
c) determining attractive meat products that may be produced from the carcass based on the found quality characteristics and possibly other data,
d) recording the identity of the carcass and the attractive meat products that may be produced, as well as any other data, in a database, together with corresponding information on other carcasses on the slaughterline, and
e) selecting carcasses from the database for production of attractive meat products.

Selection preferably takes place within 24 hours of slaughter.

The measurements are preferably carried out on a whole carcass.

If desired, one or more external anatomical parts of a carcass may be measured, and these measurements may be used when measuring internal parts and/or when determining quality characteristics of the carcass based on the measurements and possibly other data.

The measurements may for instance be carried out in a facility comprising three modules: a preliminary examination station (external parts), CT measuring equipment (internal parts/surface parts) and a recording and calculation station with automatic/manual input on market parameters for producing plans as to use of the carcasses, on which the measurements are made. The quality characteristics, and the plans that are made based on these, may then serve to sort the carcasses from which, according to the plan, the most attractive meat products are produced. With the method in question, the measuring rate should be so high that the production on the slaughterline is not reduced, i.e. in practice is should be at least 400 and ideally up to 1300-1500 carcasses per hour.

In a further development of the method, meat products are produced from the selected carcasses. The method for producing meat products from carcasses on a slaughterline comprises:
a) measuring internal anatomical parts of the carcass,
b) determining quality characteristics of the carcass based on the measurements and possibly other data,
c) determining attractive meat products that may be produced from the carcass based on the found quality characteristics,
d) recording the identity of the carcass and the attractive meat products that may be produced, as well as any other data, in a database, together with corresponding information on other carcasses on the slaughterline,
e) selecting carcasses from the database for production of attractive meat products.
f) cutting these carcasses into pieces suited for production of the selected attractive meat product(s), and
g) processing these pieces into the selected meat product(s).

Cutting the carcass into pieces may be controlled by the measurement of one or more external and/or internal anatomical part(s).

In an additional aspect of the invention, a database is used for automatically determining quality characteristics of a carcass on a slaughterline. The method comprises:
a) providing a database comprising models of types of carcasses by CT measurement of the nature of internal anatomical parts of carcasses in several cross-sections in each carcass, each model having associated quality characteristics/-parameters for said model, b) CT measuring the nature of internal anatomical parts of a carcass on the slaughterline in at least one cross-section in the carcass but in fewer cross-sections than were used per carcass in step a) for constructing the database, c) selecting the model from the database where there is the best correlation between the nature of internal anatomical parts of the carcass in one or more of the cross-sections measured in step b) and the nature of internal anatomical parts in the corresponding cross-section of the model, and d) extracting from the database recorded quality characteristics/parameters for the selected model.

The CT measurement in step a) of the nature of internal anatomical parts of carcasses in several cross-sections in each carcass may comprise measurement of more than 50% by volume of the carcass.

The CT measurement in step b) may comprise less than 50% by volume of the carcass, preferably between 1 and 20% by volume.

Each model in the database may comprise a virtual representation of the type of carcass, where regions with muscles, fat and bones as well as any other tissue types are mapped, and each model may have other associated quality characteristics, such as lean meat contents, fat thicknesses, weight and bone masses.

By means of the virtual representation, each model in the database may have associated product types that may be made from the said model by cutting and processing the carcass.

The product types may be provided by virtual cutting and processing the virtual representation of said model so that the product types correspond to those which are defined in product catalogues from meat producing companies, authorities or others, or which are market relevant.

In yet another aspect of the invention, a database is used for selecting attractive product types that may be produced from carcasses on a slaughterline. The use comprises providing a database comprising models of types of carcasses obtained by CT measurement of the nature of internal anatomical parts of carcasses in several cross-sections in each carcass, and a virtual representation of each model with regard to muscles, fat and bones as well as any other tissue types, associating with each model quality characteristics and product types generated by virtual cutting and processing the virtual representation of the model with regard to predetermined or desired product specifications, measuring on-line on a slaughterline the nature or quality characteristics of a carcass on the line, and selecting, based on the measurement and the information of the database, attractive product types that may be produced from the carcass on the slaughterline.

After selection of the attractive product types that are to be produced from a given carcass in subsequent production, a separation, cutting or trimming, and/or sorting or marking of the carcass or parts thereof produced by separation and/or processing may be made in accordance with the selection.

Hereby, CT measurement may be made of the nature of internal anatomical parts of the carcass on the slaughterline in one or more cross-sections in the carcass, and the product types provided in subsequent production/processing of the carcass are thus the product types in the model that best match the CT measurement.

In the following, the invention will be described by means of examples and preferred embodiments. Reference is made to the drawings, in which.

PRELIMINARY EXAMINATION UNIT AND ANATOMICAL REFERENCE PART

Figure 1:
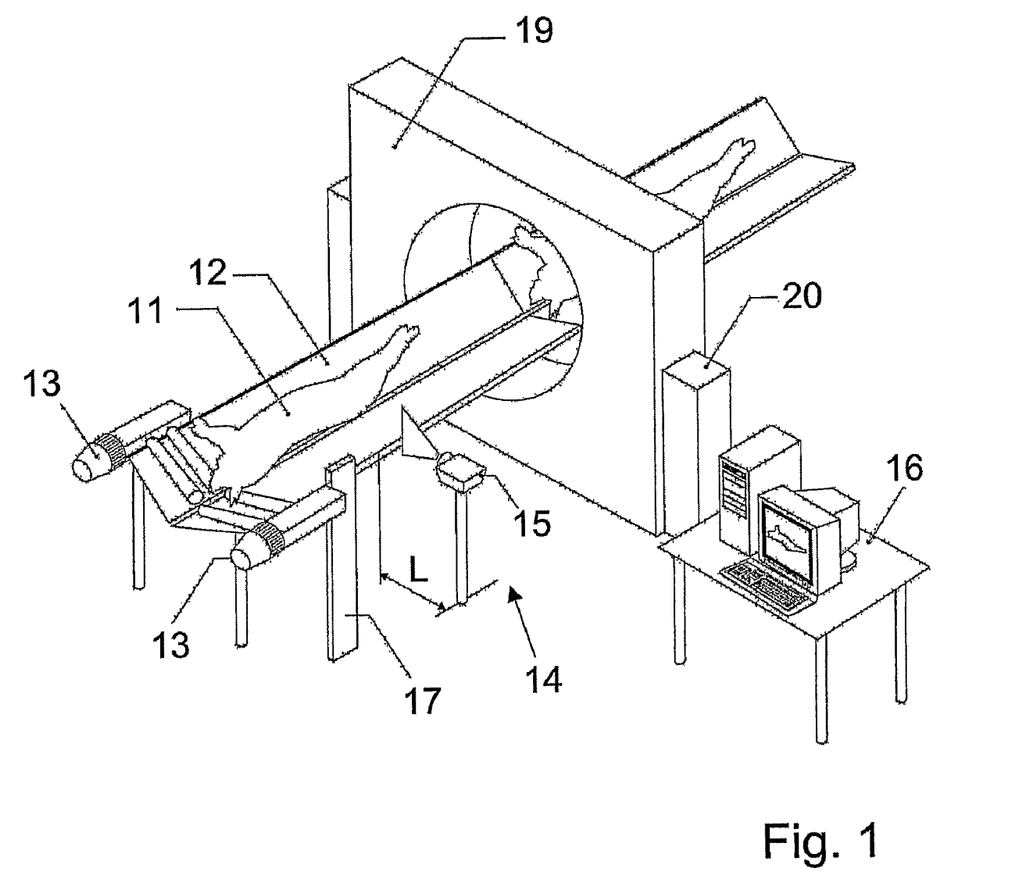
FIG. 1 shows an embodiment of a facility according to the invention for determining quality characteristics of a carcass.

The facility in FIG. 1 comprises a conveyor belt 12 which is driven by a motor 13 and conveys a carcass 11 to a preliminary examination unit 14 with a camera 15. The carcass is placed on and preferably secured to the conveyor belt and assumes a certain position relative to at least one reference point (not shown) on the belt.

The reference point may be a marking of the conveyor belt at the edge of the belt. The marking may be sensed by a suitable sensor, e.g. an optical sensor receiving reflected light from a reflector. The marking may contain a code stating a more exact position on the belt so that this position on the belt may be identified.

In another embodiment, the carcass may be placed on a transporter (not shown) conveyed by a continuously running transporter system. A transporter with the carcass may temporarily be made to perform a slow movement or may be brought to a standstill during the preliminary examination and/or the subsequent examination. This allows the influence of the carcass movement on determining the location of the anatomical reference part to be reduced or eliminated, while a high rate of transport for carcasses may be used in other places.

In an embodiment, the positions of the conveyor belt are determined using the revolutions of the motor. In another embodiment, a control unit receives signals on the movement of the at least one reference point of the conveyor belt from a monitoring unit 17. This allows the positions of the conveyor belt and thus the positions of the carcass during transport to be accurately determined. In an additional embodiment, the positions of the conveyor belt are determined using both the revolutions of the motor and measurement of the reference points of the conveyor belt.

In a preferred embodiment, movement of the conveyor belt is detected by measuring the connection between time and place, speed and acceleration, which allows the location of anatomical parts to be accurately predetermined for a later point of time and place, when the relevant piece of the conveyor belt with the carcass has been moved further down the line. The movement of the conveyor belt may be controlled and possibly corrected by controlling the revolutions of the motor and by measuring the positions of the reference points of the conveyor belt. To determine the position of the carcass relative to a known point on the belt, the camera 15 records a digital image of the carcass or part thereof. The point in time when the image was recorded is registered to determine where on the time-place-curve the carcass is located.

The image is forwarded to an image processing unit; here shown as part of a computer 16. The distance L from the camera to the conveyor belt and the extent of the visual field of the camera are known, so that the distances on the image, possibly by means of calibration, may be translated to distances between parts of the carcass. Distances may also be determined relative to the at least one reference point on the conveyor belt, so that the location of one or more anatomical reference parts of the carcass may be determined using the image relative to at least one reference point on the conveyor belt. The camera may be adapted for recording images at appropriate wavelengths, e.g. in the visible spectral range. Visible light will provide an image of external anatomical parts.

The image of the camera is processed for recognition of one or more predetermined anatomical reference parts. The image processing may be carried out in a known way, for instance by comparing a known pixel pattern of a given anatomical part recorded from a standard carcass with pixel patterns of the measured carcass. When the standard pixel pattern corresponds to the corresponding pixel pattern for the anatomical part of the carcass, the position is determined relative to the reference point on the conveyor belt. The location of the anatomical reference parts of the carcass is thus determined relative to the at least one reference point of the conveyor belt. By calibrating the location of anatomical parts relative to one or more anatomical reference parts for a number of representative carcasses, e.g. using manual measuring, the location of any anatomical part may be found relative to the reference point of the conveyor belt. For certain anatomical parts, especially the anatomical parts measurable by mechanical sensors, the location of the anatomical parts may be directly measured and need not be based on calibration from several representative carcasses. When the conveyor belt is moved to a second position, the location of the anatomical parts is determined relative to the reference point of the conveyor belt. The internal examination unit 19 (the CT measuring equipment) may thus be activated to perform cross-section measurement of the carcass when the desired anatomical part is within the measuring area of the equipment. As new anatomical parts enter the measuring area, these may, if desired, be measured by the equipment, so that measurements are made during carcass passage of the equipment in a number of cross-sections at the desired anatomical locations.

The image processing unit of the CT measuring equipment and the control unit may be units that are separated from one another, or they may be a combined unit, e.g. be part of the computer 16.

Figure 2:
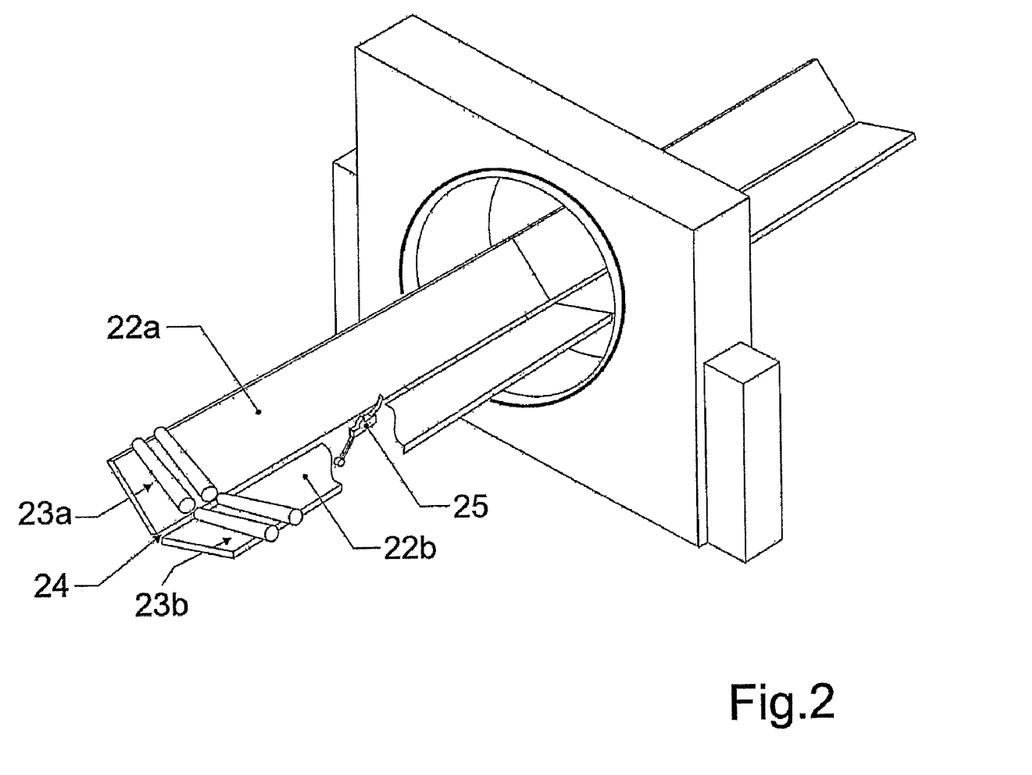
FIG. 2 shows a second embodiment of a facility according to the invention with a mechanical preliminary examination unit.

The embodiment in FIG. 2 of a facility according to the invention comprises a mechanical preliminary examination unit. The conveyor belt 22 or the transporter, its movement and control hereof are as described for the embodiment in FIG. 1 where the preliminary examination is based on measurement with a camera. The same is true for the description of the calibration of the location of the anatomical parts relative to the anatomical reference part.

The preliminary examination unit comprises a mechanical tail head sensor 25 arranged in an opening between two tilted parallel conveyor belts 22a and 22b. Orientation devices 23a and 23b, shown here as two sets of tilted rollers with an opening 24 between them, ensure that the carcass (here a pig carcass) is turned so that the tail is taken up in the opening 24 and stays in the opening between the conveyor belts when the carcass is transported by these. This provides a simplified way of fixing the location of the carcass on the conveyor belts without securing the carcass to the actual conveyor belt, while the tail head is made available for detection with the tail head sensor when the carcass passes this. In this embodiment the tail head thus serves as an anatomical reference part.

This embodiment may also comprise mechanical sensors known per se for other anatomical parts, e.g. sensors for snout, foreleg/elbow, groin, or pubic bone. A jaw sensor is disclosed in EP 1 135 988.

The tail head sensor and other mechanical sensors may, if desired, be used in connection with the transporter and the transporter system, which is mentioned in the description of the embodiment in FIG. 1.

The tail head sensor 25 in FIG. 2 is shown as being located before the internal examination unit 19. If desired, it could, however, be placed immediately after the internal examination unit if the carcass is transported with the tail furthest ahead in the direction of transport.

In a third embodiment (not shown), the preliminary examination unit comprises an X-raying facility and a detector capable of measuring changes in the absorption and/or the intensity of X-radiation when this penetrates of scatters in the carcass. The carcass is conveyed to a first measuring position in the preliminary examination unit. The radiation is directed towards the carcass, and the transmitted or scattered radiation is measured in a predetermined direction. The direction may for instance be in the direction of transmission, in a direction to the side, in a direction directly rearwards, or in directions there between. The carcass is then conveyed another distance, and the measurement is repeated. This stepwise measuring process is continued, until e.g. a characteristic change is registered for an anatomical part. Moreover, the carcass can be continuously conveyed during and between the measurements. Anatomical reference parts which may be measured with X-radiation are visible anatomical parts as well as internal anatomical parts, or boundaries between these. Internal anatomical reference parts for instance comprise bones and transitions between muscular tissue and osseous tissue. The characteristic change in the penetrating or scattered radiation may be determined by calibration for the individual anatomical parts. If determination of the location of two or more anatomical reference parts is desired, combinations of the disclosed detector types may be used, e.g. vision combined with one or more mechanical sensors.

Movement of the Conveyor Belt

Through knowledge of the movement of the conveyor belts and knowledge of the location of the anatomical reference part(s), e.g. tail head and foreleg, distances to other anatomical parts may be determined by means of algorithms or models. This allows the location of an anatomical part to be determined for any position of the conveyor belts and at any time, e.g. when the carcass is to be examined in the internal examination unit.

The movement of the conveyor belts may be any stepwise or continuous movement ensuring that the location of the anatomical reference part is determined with the necessary accuracy at the preliminary examination. It is preferred that the conveyor belts are moving, so that detecting the location of the anatomical reference part relative to the reference points of the conveyor belt may be done during transport of the carcass through the preliminary examination unit.

In an embodiment, the mechanical method is preferred as it is both fast and simple to realize.

In another embodiment, the camera method is preferred as it is flexible with regard to selection of reference part(s). It is fast as image recognition may be done electronically.

The speed of the stepwise and/or continuous movement of the conveyor belts is calibrated with regard to the desired accuracy of the preliminary examination and the internal examination. If desired, the carcass may be transported by different conveyor belts or transport systems when examined in the preliminary examination part and the internal examination unit so that the speed may be adjusted to working conditions thereof.

Internal Examination Unit and Sectional Images

When the preliminary examination is completed, the conveyor belts forward the carcass to the internal examination unit 19.

The internal examination unit 19 has an irradiation unit with irradiation devices for sending penetrating radiation through the carcass, and a detection unit with detection devices for detecting the transmitted and/or scattered radiation in at least one direction. Absorption and/or scattering of the penetrating radiation in the carcass is determined in several directions for a cross-section of the carcass. The measuring equipment comprises a computer device that can reconstruct these measured data into a cross-sectional image of the carcass at the relevant location or into a data collection for the cross-section in question, where the different shades of grey/colours or data values represent different parts. By means of the image it is possible to calculate the size (area or thickness) of meat, fat, bone or other tissue types and the share of these tissue types or the position of these parts. By means of the data collection it is possible to determine shares of meat, fat, bone and other tissue.

X-radiation of one or more energies, e.g. 40 keV and/or 120 keV, may be used.

In an embodiment, the measuring equipment 19 comprises irradiation and detection devices arranged diametrically opposite each other (not shown) on an essentially circular periphery around the conveyor belt 12.

In another embodiment, the measuring equipment comprises an irradiation device and several detection devices that are moved simultaneously along the essentially circular periphery.

In a third embodiment, the measuring equipment comprises an irradiation device with a fan- or cone-shaped radiation, and several detection devices, together defining a detection area, and being moved along the essentially circular geometry.

As an alternative to CT measuring equipment with X-ray source, other tomographical techniques may be used, for instance but not limited to NMR, microwaves, PET or nuclear energy.

If conditions allow, the orientation of the carcass may be chosen freely relative to the longitudinal axis of the conveyor belt. It is, however, preferred that the carcass is oriented in such a way that its longitudinal axis runs along or is essentially parallel with the longitudinal axis of the conveyor belt.

It is preferred that the plane for the circular position or circular movement of the detection devices is transverse to or essentially perpendicular to the longitudinal axis of the conveyor belt, and that the normal for the plane in the centre of the circular movement mainly runs in the same direction as the longitudinal axis of the carcass. Other orientations of the plane may be used. To optimize mapping of a given internal anatomical part, orientation of the plane for the circular movement of the irradiation and detection devices may be adapted according to the type of the anatomical part.

The internal examination unit comprises a data processing and scanner control unit 20 adapted for controlling adjustment of the irradiation and detection devices, and for communicating with the computer 16 which controls the preliminary examination unit, the internal examination unit, and the interaction between them. It is preferred that the data processing and scanner unit comprises devices for reconstructing a sectional image from the measurements.

The data processing unit for reconstruction of sectional images may be part of the computer 16.

Control Unit

In the computer 16, the facility has a control unit that is adapted for communicating with the preliminary examination unit 14 and its components, e.g. the camera 15 and the motor 13.

The control unit is also adapted for processing and sending control signals to the data processing and scanner control unit 20 for the internal examination unit 19. The control signals may exercise control either directly or indirectly. With indirect control, the unit is autonomous once it has received a start signal. For example, the CT measuring equipment may, upon a start signal, perform a measuring sequence comprising measuring a predetermined number of measurements in different angles. When the measurement is completed, a termination signal is sent to the control unit, which may then initiate processing of the obtained data, e.g. reconstruction of a sectional image from the obtained measurements.

The time for commencing measurement, or the position of the conveyor belt when the carcass has reached the measuring position is given by the location of the internal anatomical part to be measured and the location of the anatomical reference part as well as the movement of the conveyor belt.

The control unit preferably comprises at least one computer for receiving, processing, and sending control signals to the internal examination unit and/or the data processing unit.

Figure 3:
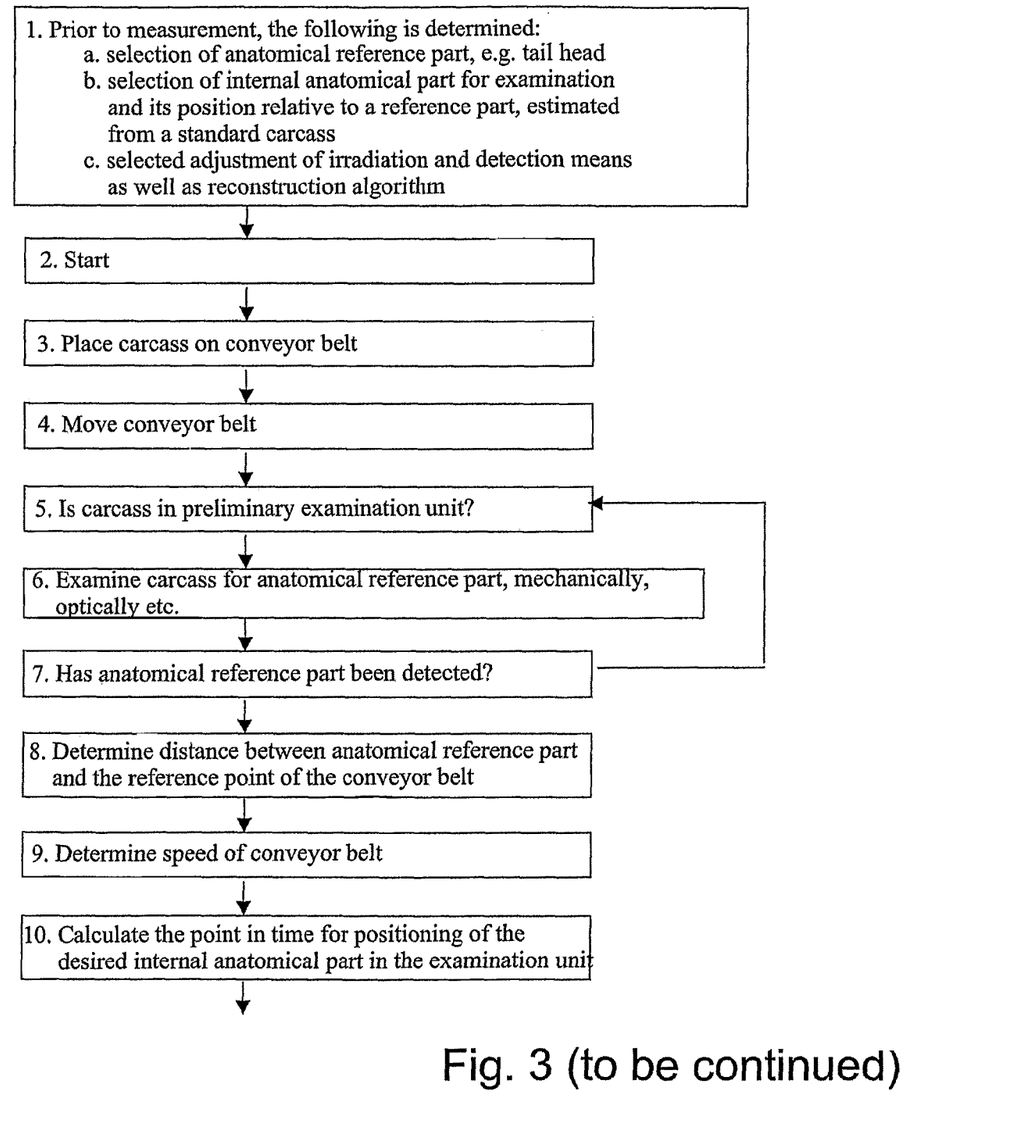
FIG. 3 shows a flow chart for a sequence of process steps when practising the method of the invention.

The control unit preferably comprises one or more programs with instructions for the respective control units to carry out the actions of the facility of the invention, shown in FIG. 3.

Prior to measurement, the position of the reference part(s) must be measured and the position(s) of the internal anatomical part(s) must be calculated. When the carcass on the conveyor belt has reached the preliminary examination unit, the position of the reference part(s) is determined relative to the reference point of the belt. From this determination, the position of the internal anatomical part(s) is calculated using an algorithm or a model. Using knowledge of for instance the conveying speed of the belt, the calculation unit may determine the point of time when the internal anatomical part has reached the measuring equipment, so that measured data may be recorded and a cross-sectional image of the internal anatomical part may be reconstructed from measured data. Instead of the conveyance of the belt, other systems may be used for keeping track of the immediate position of the carcass, e.g. marks on the belt or the transporter that are read in strategically placed reading stations.

If recording of more cross-sectional images is desired, the measuring procedure is repeated when the carcass has moved a pre-calculated distance and a predetermined anatomical part is in position for measurement in the CT measuring equipment. In this way, a number of cross-sectional images may be recorded which may be used as a basis for determining quality characteristics. If several cross-sectional images are recorded, these may be compared to cross-sectional images in a catalogue on carcasses, the build and quality characteristics of which are already known. The cross-sectional images that collectively provide the best match for a carcass in the catalogue show the most likely build of the carcass and thus reveal the quality characteristics of the carcass in question, e.g. lean meat content, fat thickness on loin, etc. Based on the knowledge provided on the carcass in the catalogue, further use of the carcass in production and sales may be planned and carried out, e.g. when cutting half pig carcasses into front end, middle and ham piece, and further processing of these into cuts, and/or when sorting carcasses/ carcass parts for different applications. Through reference information from the catalogue, and/or when calculating formed/previously known data, knowledge may also be gained on the lean meat content of the carcass for use in settlement with the manufacturer who delivered the animal for slaughter.

Cross-Sectional Image of a Whole Pig Carcass

By means of CT measuring equipment, an image 60 (see FIG. 6) was obtained of a cross-section of a whole pig carcass, 57 cm in the longitudinal axis of the carcass from the tail head. The distance was chosen so as to be able to assess the size and the shape of essential internal parts, e.g. abdominal muscles 61, liver 64, intestines 63 with contents 62, lung apices 70, spine 66, ribs 67a and 67b, as well as M. Longissimus Dorsi 65 and associated support muscles 68a and 68b, and the subcutaneous fat layer 69. The location of the section is based on a catalogue on the location of anatomical parts, e.g. established by manual measurement with measuring tape on a large number of representative carcasses and/or animals. In larger or smaller carcasses the corresponding cross-sections will be proportionally further from and nearer to the tail head, which may be calculated by means of appropriate algorithms. The variation in linear measures for typical slaughter pigs is in the range of 5-25%.

When a pig carcass passes the preliminary examination unit in the facility of the invention, the tail head is detected with the tail head measuring device. Movement of the conveyor belt is measured and controlled, and when the time and place for the conveyor belt is reached when the desired cross-section is in the target position in the CT measuring equipment, scan of the carcass is initiated. A given number of projections is measured, e.g. 704 projections during a complete rotation of X-ray source and detector. By "a projection" is meant a measurement of the direct X-radiation. Preferably, this is measured via a collimator removing contributions from scattered X-radiation.

Using the projections, a reconstruction algorithm, e.g. the program AR AH3 h17.smo developed for Siemens AR.T scanner, calculates a cross-sectional image of the carcass. On the cross-sectional image it is determined which pixels represent the different tissue types, e.g. meat and fat and bones, as well as guts such as intestines with contents. For this a standard image analysis is used known by those skilled in the art, e.g. image segmentation (MatLab Image Toolbox MAT-LAB® 6.5 Image Processing Toolbox 5.0, The Matworks, Inc., USA).

If desired, more CT sectional measurements may be performed, lying side-by-side or being spaced apart from one another. If convenient, a 3D model hereof may be constructed. The sectional images may be used collectively to point out the type of carcass that best matches the carcass, or a sectional image may be selected as the most representative of the whole carcass from certain quality characteristics of the carcass, such as the positions in which the carcass may be divided.

Determining Total Lean Meat Content

Figure 6:
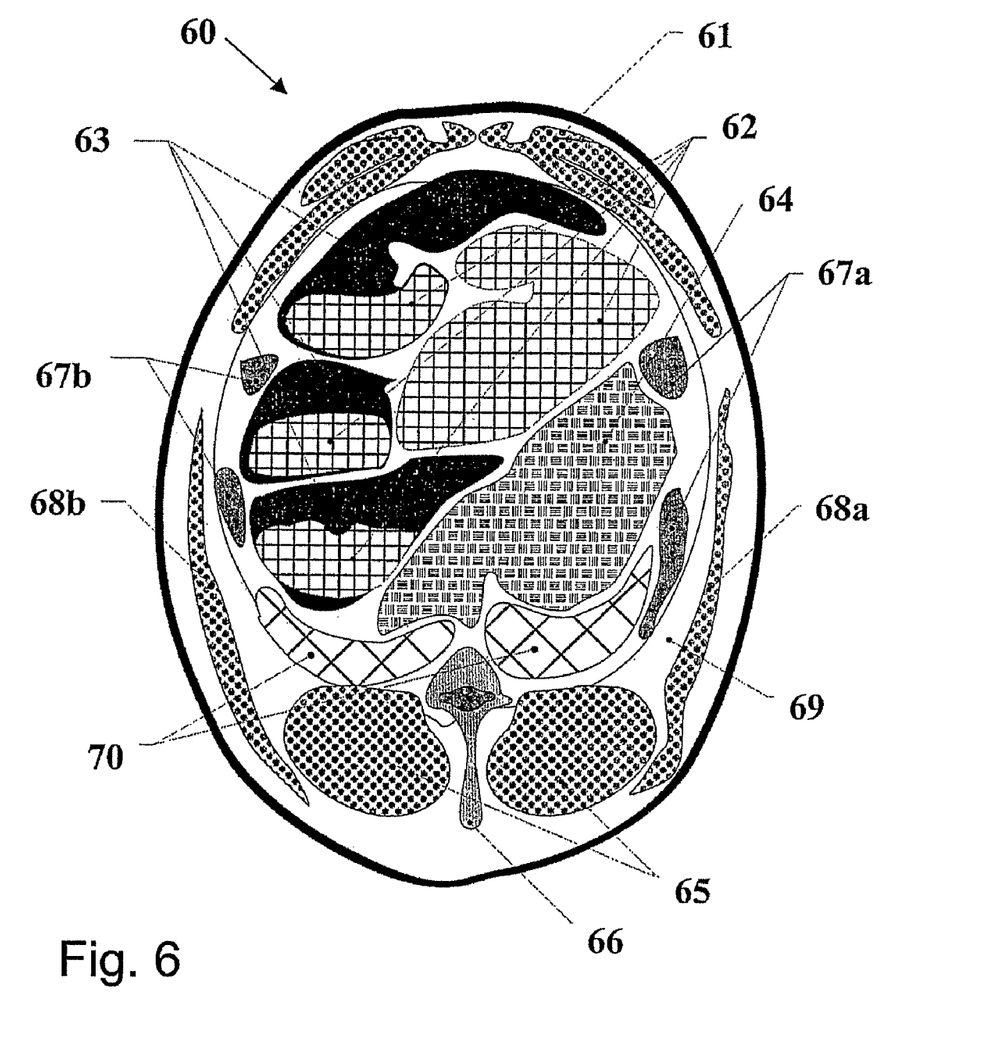
FIG. 6 shows a cross-sectional image of a whole pig carcass obtained by computed tomography and FIG. 7 shows a diagram of a production planning system which is based on on-line measurement of characteristics of carcasses on a slaughterline.

If a sectional image, as shown in FIG. 6, has parts removed that do not figure as slaughter-wise interesting parts, e.g. guts, essential data on the carcass, e.g. the total lean meat content for whole pig carcasses or parts hereof, may be estimated by means of a multivariate model.

Figure 4:
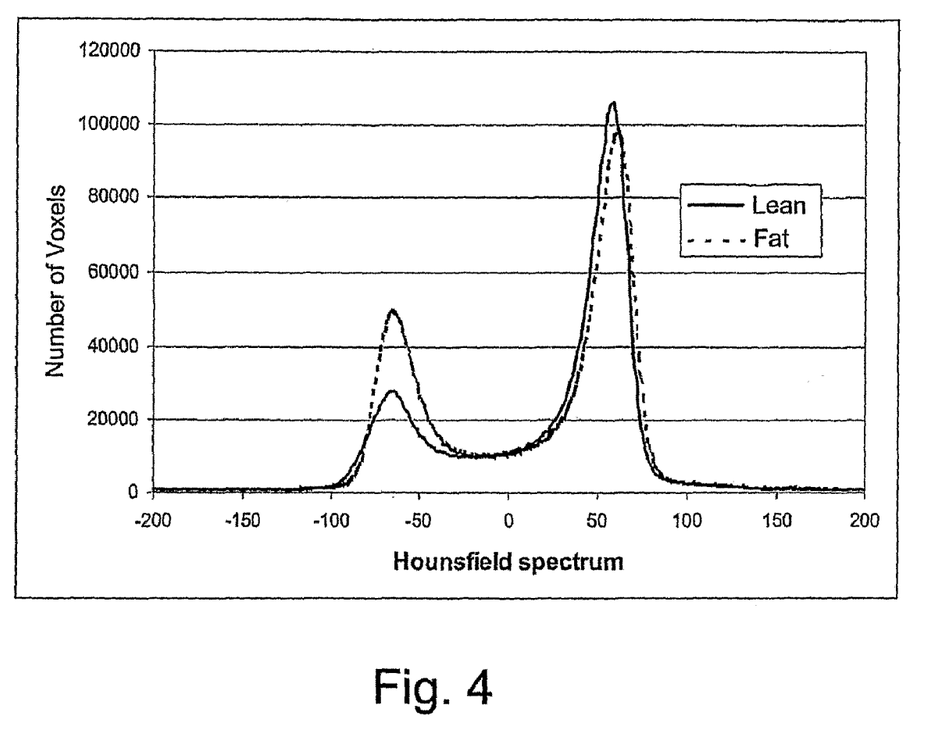
FIG. 4 shows Hounsfield spectrums for cross-sections of a fat and a lean pig carcass.
Figure 5:
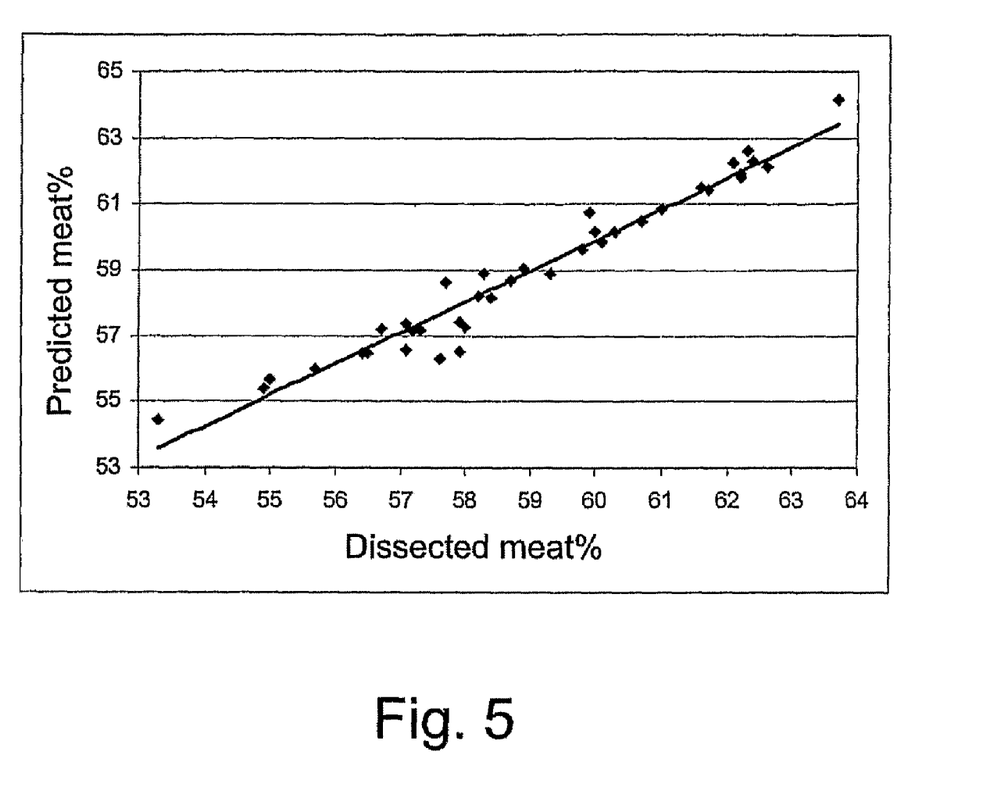
FIG. 5 shows a comparison between lean meat contents estimated from Hounsfield spectrums and lean meat contents provided by dissecting 40 pig carcasses.

The lean meat content of a carcass may be measured with great accuracy by using the frequency distribution of pixels in the cross-sectional image expressed as their Hounsfield value together with a reference curve for lean meat contents. In FIG. 4, a Hounsfield spectrum is shown for a fat and for a lean pig carcass. FIG. 5 shows a reference curve for predicted lean meat content based on manual dissection of 40 pig carcasses and recording of 130 CT sectional images for each of these carcasses.

By means of a CT image and the reference curve, estimates of the total lean meat content for a single carcass could be obtained with a correlation of 0.97 and an error of prediction (Root Mean Square Error of Prediction RMSEP) of about 0.65%. This is a considerable improvement compared to the best, currently used measuring equipment for determining lean meat content.

Sorting and Production Planning

Quality characteristics of carcasses/parts that are obtained by measuring whole carcasses before they are opened may very advantageously be used as input in production planning of the slaughterhouse. When data has been collected for a suitable number of carcasses, the plan is made for cutting up/cutting out each carcass by combining measured quality characteristics with, in particular, volume of orders, prices and quantities. Suitably, a preliminary plan of use for the carcasses is prepared, and pre-sorting is carried out (separating the carcasses according to quality characteristics). At the end of the slaughter day the plan of use may be updated.

The same method may be used on half carcasses or on parts after cutting/trisectioning. If parts are measured, very detailed information is gained which may be used for adjusting the plan of use for the part and/or adjusting cutting robots and derinding/fat trimming machines for processing the parts.

The plan of use for a carcass depends on the quality characteristics of the individual parts. Due to logistical reasons, pre-sorting will often be done on the basis of quality characteristics of one of the parts. The final use of the parts is then determined after the carcass has been cooled and cut into three to four parts. Pre-sorting may, in other cases, be done on the basis of quality characteristics of several of the parts.

At the individual subject level, traceability may be difficult to maintain after cutting. It may thus be appropriate to repeat the measurements on the parts according to the same measuring principle. These measurements will be able to provide such detailed information on muscle shape and fullness, as well as the shape and extent of the fat layer, that they may control the subsequent cutting robots and derinding/fat trimming machines. It may also be relevant to adjust the plan of use after such measurements. If the loin piece from a middle piece is planned for backs, a detailed measurement may adjust derinding and trimming to the quality (defined by the thickness of the fat layer and the meat-fat-distribution) which is in part optimal for the product and in part constitutes the demanded product.

The "Catalogue Solution"

Figure 7:
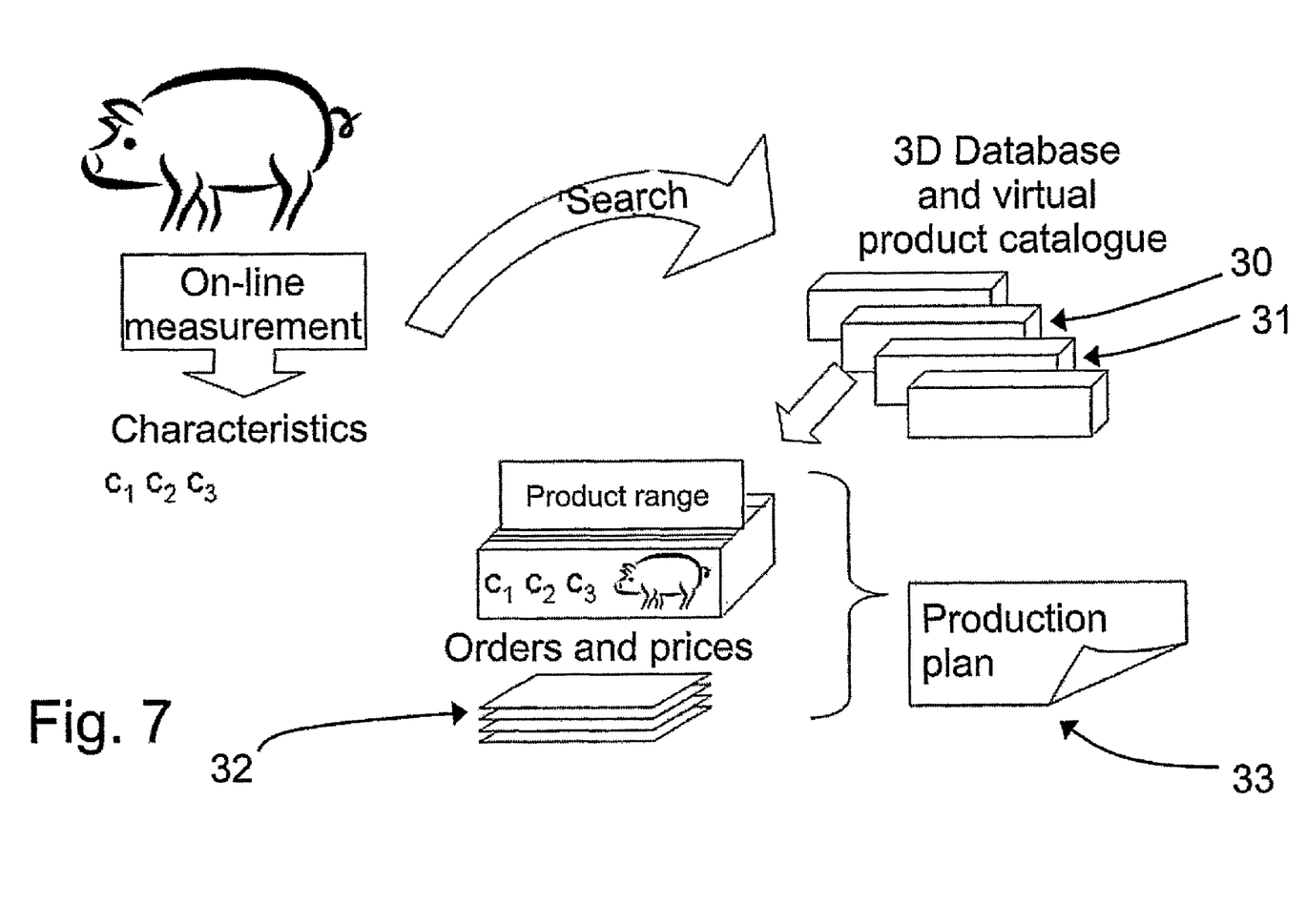

One possible solution for production planning comprises setting up a database with information on different carcasses and their properties, as well as on-line measurement of certain properties of the individual carcasses on the slaughterline. The measured properties may then be used for "searches" in the database, whereby more detailed information for use in production planning may be obtained. The system is outlined in FIG. 7 and may for instance comprise:

a database 30 with 3D models of a representative sample of the pig population established with standard CT equipment. Each 3D model is identified by means of a number of characteristics that may also be measured automatically on the slaughterline, and the database 30 may be regularly updated with new 3D models representing the population.

a virtual product catalogue 31 which enables yield assessment and which may also be regularly updated with new product combinations. The virtual product catalogue 31 comprises virtual product ranges "cut" from each 3D model with accompanying quality and yield assessment.

a link to an order/price system 32, e.g. the current order book of the company and a price optimisation program.

on-line measuring equipment for measuring certain characteristics.

On-line measurement consists of measuring specific characteristics that may be used to identify the 3D model in the database 30 that best corresponds to the carcass in question. As soon as a 3D model from the database 30 is associated with the measurement in question, different quality characteristics may be determined, and the production plan 33 may be established based on experiences regarding the identified model as well as the current order/price data.

The specific characteristics may comprise measured outer characteristics (length, circumference, etc.) from a pre-treatment or measuring station, and measured inner characteristics determined by means of a small number of CT sections (slices). The position of the individual CT sections is given by the fixed points determined in the pre-treatment station. Additional characteristics are obtained by means of the 3D model based on measured characteristics.

Examples of Specific Characteristics

A possible system solution is based on relatively few CT sections which will be able to provide information on the length and circumference of the back muscle, the thickness of the fat layer around the entire carcass at given anatomical sites, meat/fat-distribution in the breast part, and the circumference and length of the ham. This information is expected to be able to characterize the entire carcass so that information from a carcass with approximately the same characteristics as what was measured may be used on the carcass in question.

The "Calibration Solution"

On-line measurement is carried out as in the "catalogue solution". Instead of a database, decision support is based on calibration. This means that the quality is determined by means of mathematical models with the measured characteristics as input and the quality as output. The plan of use for the individual carcass is determined (possibly off-line) in a parallel order/price system where quality is input.

The "On-Line 3D Solution"

This solution requires/uses new high speed CT technology translated into industrial CT, as well as high speed computers, for on-line analysis at the slaughter/production line. If these prerequisites are present, this solution will be optimal with regard to information level.

The solution establishes a 3D model on-line by means of on-line CT. Instead of a virtual product catalogue, a virtual cut is carried out directly on the measured 3D model in addition to establishing the optimum use.

In the "On-line 3D solution" much or all of the information on the carcass is available—including information that can be used as detailed input for cutting robots regarding cutting sites and courses. If measurements were made on a hot carcass, deformation from the hot to the cold carcass is preferably taken into account.

The "Part Solution"

If measurements on parts are desired, a smaller version of the two above-mentioned solutions for carcasses may be constructed as an on-line solution. For instance, measurements may be made on the middle piece after cooling and trisectioning. The information may be used directly (calibration) or via searches in a middle piece database to establish a quality goal for the middle piece, e.g. the thickness of the fat layer (the fat cap) around the carcass.

The invention claimed is:

1. A method for automatically determining quality characteristics of a carcass on a slaughterline, said carcass comprising one or more anatomical reference parts, said method comprising:
   a) conveying the carcass in a direction of transport,
   b) preliminary examination to determine a location of said one or more anatomical reference parts of the carcass in the direction of transport,
   c) calculating a location in the direction of transport of at least one cross-section in the carcass using the location of the anatomical reference part(s) and possibly other data on the carcass, and
   d) CT measuring the nature of internal anatomical parts of the carcass in at least one of these cross-sections in the carcass, controlled by the calculated location.

2. A method as claimed in claim 1, wherein the reference part(s) comprise(s) an externally detectable anatomical part, including a foreleg, an elbow, an armpit, a groin, a tail/tail head, or a pubic bone.

3. A method as claimed in claim 1, wherein the location in the direction of transport of the at least one cross-section of the carcass is calculated by means of an algorithm or a model using the location of the reference part(s).

4. A method as claimed in claim 1, wherein the CT measurement of the nature of internal anatomical parts of the carcass comprises measurement of less than 50% by volume of the carcass, preferably between 1 and 20% by volume.

5. A method for the production of meat products from carcasses on a slaughterline, said method comprising a method according to claim 1 for automatically determining a quality characteristics of a carcass on said slaughter line, wherein said method for the production of meat products from carcasses on a slaughterline comprises the further steps of:
   e) measuring internal anatomical parts of the carcass,
   f) determining quality characteristics of the carcass based on the measurements and possibly other data,
   g) determining attractive meat products that may be produced from the carcass based on the found quality characteristics,
   h) recording the identity of the carcass and the determined attractive meat products that may be produced, as well as any other data, in a database, together with corresponding information on other carcasses on the slaughterline, and
   i) selecting carcasses from the database for production of selected attractive meat products.

6. A method as claimed in claim 5, wherein the measurements are made on a whole carcass.

7. A method as claimed in claim 5, wherein the location of one or more external anatomical parts of a carcass in the direction of transport are measured, and these measurements are used when measuring internal anatomical parts and/or when determining quality characteristics of the carcass.

8. A method as claimed in claim 5 for producing meat products from carcasses on a slaughterline, said method further comprising:
   j) cutting these carcasses into pieces suited for production of the selected attractive meat product(s), and
   k) processing these pieces into the selected meat product(s).

9. A method as claimed in claim 8, wherein the cutting of the carcass into pieces is controlled by the measurement of one or more external and/or internal anatomical part(s).

* * * * *